(12) United States Patent
Haas et al.

(10) Patent No.: US 7,612,221 B2
(45) Date of Patent: Nov. 3, 2009

(54) PRODUCTION OF FATTY ACID ALKYL ESTERS

(75) Inventors: Michael J. Haas, Oreland, PA (US); William N. Marmer, Fort Washington, PA (US); Thomas A. Foglia, Lafayette Hill, PA (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 304 days.

(21) Appl. No.: 11/337,458

(22) Filed: Jan. 23, 2006

(65) Prior Publication Data
US 2006/0155138 A1    Jul. 13, 2006

Related U.S. Application Data

(63) Continuation-in-part of application No. 10/886,246, filed on Jul. 7, 2004, now abandoned, which is a continuation-in-part of application No. 10/404,409, filed on Apr. 1, 2003, now abandoned.

(60) Provisional application No. 60/369,370, filed on Apr. 2, 2002.

(51) Int. Cl.
*C07C 51/43*    (2006.01)

(52) U.S. Cl. .................................................. 554/174
(58) Field of Classification Search .................. 554/174
See application file for complete search history.

(56) References Cited

U.S. PATENT DOCUMENTS

| 7,112,229 | B2* | 9/2006 | Khalil et al. ............... 44/308 |
| 2003/0032826 | A1* | 2/2003 | Hanna ....................... 554/124 |
| 2005/0011112 | A1 | 1/2005 | Khalil et al. |
| 2005/0274065 | A1 | 12/2005 | Portnoff et al. |

FOREIGN PATENT DOCUMENTS

WO    WO2005014765    2/2005

OTHER PUBLICATIONS

English Translation of FR -2,784,116.*

* cited by examiner

*Primary Examiner*—Deborah D Carr
(74) *Attorney, Agent, or Firm*—John D. Fado; G. Byron Stover

(57) ABSTRACT

The present invention relates to a method for producing fatty acid alkyl esters, involving transesterifying a feedstock containing lipid-linked fatty acids with an alcohol and an alkaline catalyst to form fatty acid alkyl esters. The feedstock has not been previously treated to release the lipid components of said feedstock, or the feedstock has been previously treated to release lipid components and the feedstock contains residual lipids (e.g., <about 30% of the original content of lipids).

49 Claims, 7 Drawing Sheets

1  2  3  4  5  6  7  8  9

1 2 3 4 5 6 7 8 9 10 11 12

PRODUCTION OF FATTY ACID ALKYL ESTERS

REFERENCE TO RELATED APPLICATION

This patent application is a continuation-in-part of U.S. patent application Ser. No. 10/886,246, filed on 7 Jul. 2004, which is a continuation-in-part of U.S. patent application Ser. No. 10/404,409, filed on 1 Apr. 2003, which claims the benefit of U.S. Provisional Application No. 60/369,370, filed 2 Apr. 2002. The subject matter of these related applications are incorporated herein by reference in their entirety.

BACKGROUND OF THE INVENTION

The present invention relates to a method for producing fatty acid alkyl esters, involving transesterifying a feedstock containing lipid-linked fatty acids with an alcohol and an alkaline catalyst to form fatty acid alkyl esters. Generally, the feedstock has not been previously treated to release the lipid components of the feedstock, or the feedstock has been previously treated to release lipid components yet the feedstock contains residual lipids (e.g., <about 30% of the original content of lipids).

Over the past three decades interest in the reduction of air pollution, and in the development of domestic energy sources, has triggered research in many countries on the development of non-petroleum fuels for internal combustion engines. For compression ignition (diesel) engines, it has been shown that the simple alcohol esters of fatty acids (biodiesel) are acceptable alternative diesel fuels. Biodiesel has a higher oxygen content than petroleum diesel, and therefore reduces emissions of particulate matter, hydrocarbons, and carbon monoxide, while also reducing sulfur emissions due to a low sulfur content (Sheehan, J., et al., Life Cycle Inventory of Biodiesel and Petroleum Diesel for Use in an Urban Bus, National Renewable Energy Laboratory, Report NREL/SR-580-24089, Golden, Colo. (1998); Graboski, M. S., and R. L. McCormick, Prog. Energy Combust. Sci., 24:125-164 (1998)). Since it is made from agricultural materials, which are produced via photosynthetic carbon fixation (e.g., by plants and by animals that consume plants), the combustion of biodiesel does not contribute to net atmospheric carbon levels.

Initial efforts at the production, testing, and use of biodiesel employed refined edible vegetable oils (expelled or recovered by solvent extraction of oilseeds) and animal fats (e.g., beef tallow) as feedstocks for fuel synthesis (Krawczyk, T., INFORM, 7: 800-815 (1996); Peterson, C. L., et al., Applied Engineering in Agriculture, 13: 71-79 (1997); Holmberg, W. C., and J. E. Peeples, Biodiesel: A Technology, Performance, and Regulatory Overview, National SoyDiesel Development Board, Jefferson City, Mo. (1994); Freedman, B., et al., J. Am. Oil Chem. Soc., 61(10): 1638-1643 (1984)). More recently, methods have been developed to produce fatty acid methyl esters (FAME) from cheaper, less highly refined lipid feedstocks such as spent restaurant grease and soybean soapstock (Mittelbach, M., and P. Tritthart, J. Am Oil Chem. Soc., 65(7):1185-1187 (1988); Graboski, M. S., et al., The Effect of Biodiesel Composition on Engine Emissions from a DDC Series 60 Diesel Engine, Final Report to USDOE/National Renewable Energy Laboratory, Contract No. ACG-8-17106-02 (2000); Haas, M. J., et al., Enzymatic Approaches to the Production of Biodiesel Fuels, in Kuo, T. M. and Gardner, H. W. (Eds.), Lipid Biotechnology, Marcel Dekker, Inc., New York. (2002); Canakci, M., and J. Van Gerpen, Biodiesel Production from Oils and Fats with High Free Fatty Acids, Abstracts of the 92$^{nd}$ American Oil Chemists' Society Annual Meeting & Expo, p. S74 (2001); U.S. Pat. Nos. 2,383,601; 2,494,366; 4,695,411; 4,698,186; 4,164,506; Haas, M. J., et al., J. Am. Oil Chem. Soc., 77:373-379 (2000); Haas, M. J., et al., Energy & Fuels, 15(5):1207-1212 (2001)).

One aspect of the present invention is the production of fatty acid alkyl esters using as substrate unextracted lipids still residing in the agricultural materials in which they were produced. Our method achieved the desired transesterification of the lipid-linked fatty acids by direct treatment of the lipid source itself with alcohol and an alkaline catalyst. Because no prior isolation or purification of the lipid in the lipid source was involved, this method for ester synthesis should have a greatly reduced cost compared to existing methods since it eliminates the need for costly expelling/extraction and refining steps currently employed to produce the fats and oils that are the feedstock for fatty acid ester synthesis. Our method can also be used with a feedstock that has been previously treated to release lipid components yet contains residual lipids (e.g., <about 30% of its original content of lipids).

SUMMARY OF THE INVENTION

The present invention relates to a method for producing fatty acid alkyl esters, involving transesterifying a feedstock containing lipid-linked fatty acids with an alcohol and an alkaline catalyst to form fatty acid alkyl esters. The feedstock has not been previously treated to release the lipid components of said feedstock, or the feedstock has been previously treated to release lipid components yet contains some residual amount of its original content of lipids.

DETAILED DESCRIPTION OF THE INVENTION

Figure 1:
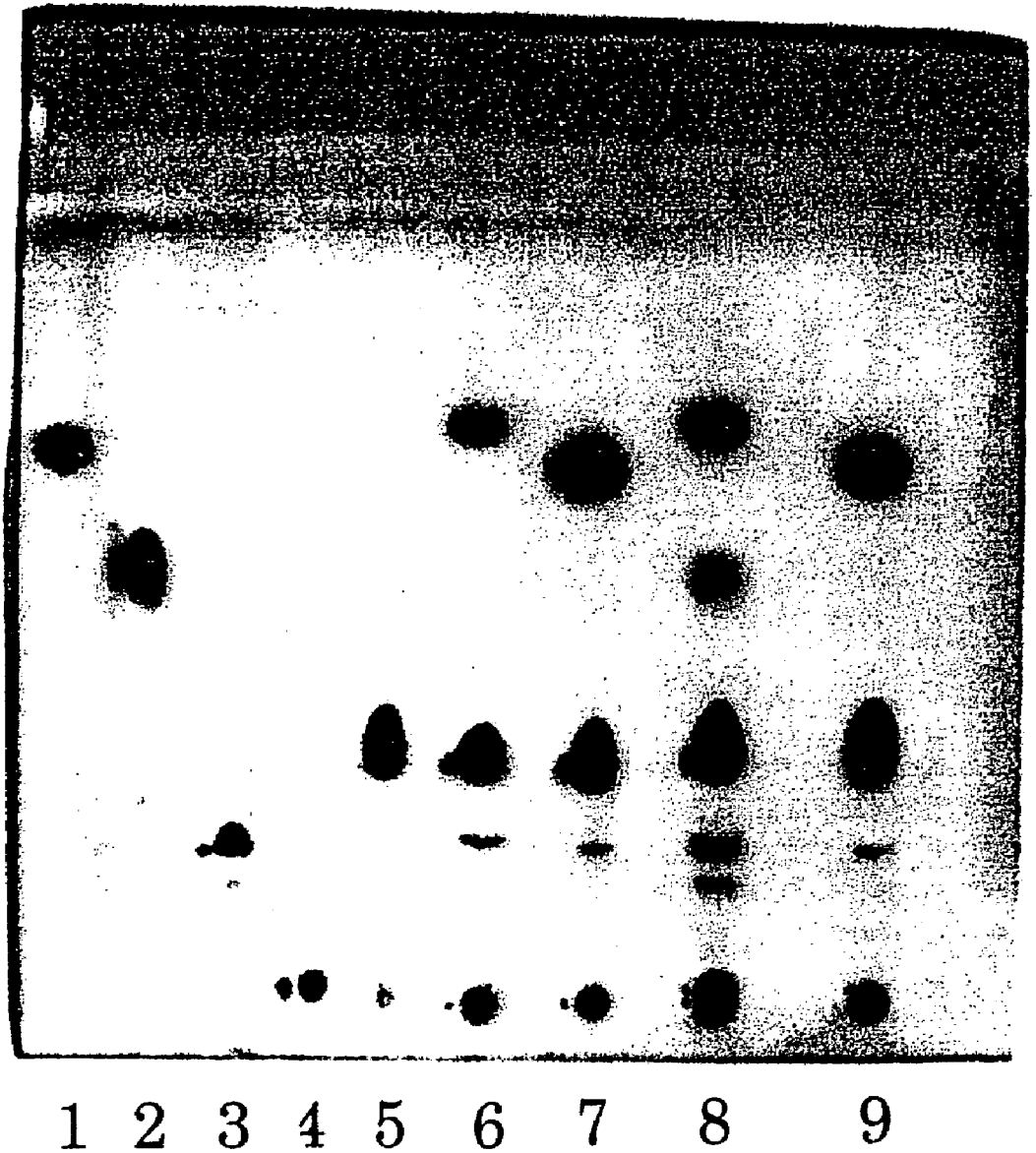
FIGS. 1-4 show the results obtained upon analysis by thin layer chromatography of the products obtained when soy flakes were subjected, under various conditions, to the method described herein.

The present invention relates to a method for producing fatty acid alkyl esters, involving transesterifying a feedstock containing lipid-linked fatty acids with an alcohol and an alkaline catalyst to form fatty acid alkyl esters. The necessity of isolating the lipid prior to its transesterification, a feature of transesterifcation technologies described in the literature, is surprisingly eliminated. The feedstock for use with this method is defined as including the following:

(1) Feedstocks that have not been previously treated to intentionally release the lipid components of the feedstock:

Intact biological sources of fats and oils from materials that usually provide a source of plant oil, including, but not limited to the intact seeds or fruits of soy, coconut, corn, cotton, flax, palm, rapeseed/canola, safflower, sunflower. The lipids in these materials are not first isolated in order for them to be utilized as feedstocks in the present invention. Generally, the intact seeds or fruits may need some pretreatment in order to expose a greater surface area or allow greater access of the reactants to the interior of the seeds or fruits which will greatly improve the efficiency and reduce the time-to-completion of the method; for example, cracking open the seeds or fruits, flaking or grinding the seeds or fruits, and other known methods. One preferred feedstock for the method of the present invention in the United States is soybeans because soybeans are the predominant oilseed processed in the United States. Generally the lipid source (e.g., oilseeds such as soy) is flaked or ground to provide additional surface area for exposure to the alcohol and alkali. For example, using soybeans as the trial feedstock (as shown below), the feedstock was flaked to approx. 0.2-2 mm in thickness and mixed in a sealed glass vessel with an alcohol (e.g., $C_{1-4}$ alcohol such as methanol, ethanol, isopropanol) and alkali (e.g., NaOH, KOH). The mixture was agitated by swirling during incubation at 60° C. or 23° C. Analysis of the liquid phase after just one hr, the briefest incubation time examined, showed fatty acid methyl esters not only to be present but to be the predominant chemical species. Thus, surprisingly, it is possible to synthesize fatty acid alky esters by direct transesterification of the lipid-linked fatty acids residing in the lipid source (e.g., oilseed). The present method surprisingly allows the production of esters from lipids that are residing in a structurally complex and heterogenous material (for example in an oilseed like soy); the feedstock has not been treated to release the lipid components of the feedstock, for example by the use of conventional organic solvent extraction or extruder-expeller technology well known in the edible oils trade. Feedstocks that have not been previously treated to intentionally release the lipid components of the feedstock are not limited to unprocessed agricultural materials described above. For example, in the production of ethanol (for beverage or fuel use) by the microbial fermentation of corn, the oil residing in each corn kernel is, in general, neither removed nor degraded; thus the solid residue following fermentation, which is known as distiller's dried grains (DDG) or distiller's dried grains with solubles (DDGS) in one favored technology of ethanol production, contains corn oil. DDG and DDGS are suitable substrates for transesterification by the methods described herein. Some might consider DDG and/or DDGS to be feedstocks under (2), or both (1) and (2), in part because DDGS can be derived by an ethanol-producing fermentation of corn which implements a technology wherein a portion of the corn oil resident in the feedstock is recovered from the corn feedstock before fermentation, or from the post-fermentation mixture, leaving a DDGS with less oil than it would have had if this prior oil recovery had not been implemented; however, as used herein, DDG and DDGS are defined as feedstocks under (1).

(2) Feedstocks that have been previously treated to release lipid components yet contains some residual amount of their original content of lipids: Lipid-bearing materials that have been previously processed in some way so that the bulk of the original lipid content has been removed; examples include lipid-containing materials of plant or animal origin such as soybean meal and the meals of other oilseeds which have been processed (e.g., extruder/expeller-treated or solvent-extracted) to remove the bulk of the lipid in the originally intact seeds or fruits, and meat and bone meal produced by the rendering of animal tissues. This feedstock is a heterogenous feedstock, one that contains other materials (e.g., protein, carbohydrate, inorganic solids, etc.) in addition to lipid. Thus the feedstock used in the present method has been previously treated to release lipid components and therefore the feedstock contains, after removal of the released lipids, less than its original content of lipids (e.g., <about 30% by weight lipids or <about 25% or <about 20% or <about 15% or <about 14% or <about 13% or <about 12% or <about 11% or <about 10% or <about 9% or <about 8% or <about 7% or <about 6% or <about 5% or <about 4% or <about 3% or <about 2% or <about 1%). In other words, the feedstock used in the present method is produced by a process involving treating an agricultural material (e.g., oilseeds) to produce free lipids and a by-product (i.e., the feedstock used in the present method) containing a fraction (e.g., <about 30% by weight lipids or <about 25% or <about 20% or <about 15% or <about 14% or <about 13% or <about 12% or <about 11% or <about 10% or <about 9% or <about 8% or <about 7% or <about 6% or <about 5% or <about 4% or <about 3% or <about 2% or <about 1%) of the total lipids in the original untreated agricultural material.

An example of the kind of material referred to in (2) above is "meat & bone meal." As a consequence of the production of meat, large amounts of animal byproduct material are generated. Such material contains the nonmarketable portions of animal carcasses, the entire carcasses of animals not fit for consumption, and butcher shop wastes. In general, this material is collected, ground, and cooked at a temperature of approximately 130° C. for at least about 20 minutes which drives off the moisture present in the material. The majority of the fat in the reaction floats to the top of the mass during this process and is subsequently removed by skimming and sold as tallow. However, some fat is unavoidably entrained in the remaining solids which are rich in protein and also contain fragmented bone. This product is termed "meat and bone meal" and is a major byproduct of the meat production industry. U.S. production in recent years has been approximately 3.3 billion pounds annually.

The feedstock for use with this method is defined as not including crude or refined isolated fats and oils, for example oils or soapstocks produced from soy, coconut, corn, cotton, flax, palm, rapeseed/canola, safflower, sunflower. The feedstock for use with this method is also defined as not including crude or refined animal products such as tallow, lard or fish oil.

Fatty acid alkyl esters may be prepared from the lipid-linked fatty acids (e.g., acylglycerides, phosphoglycerides) in the feedstock by adding an excess (in molar terms) of an alcohol and an alkaline catalyst. The alcohol may be a $C_{1-4}$ alcohol such as methanol, ethanol, isopropanol; preferably methanol or ethanol when the product is to be employed as, for example, a diesel engine fuel. The alkaline catalyst may be hydroxides, alkoxides, or carbonate of Group I and II alkali metals such as NaOH, KOH, sodium or potassium methylate or carbonate.

Transesterification will occur in virtually any volume of alcohol/alkali able to wet the ground or flaked lipid source (e.g., oilseed). Larger volumes give more complete transesterification. With regard to the amount of alkali required, when the method is conducted using the reactor geometry and reactants described herein (e.g., flaked soybeans, methanol, and alkali shaken in a sealed container incubated at 60° C.), virtually quantitative amounts of transesterification occur at a sodium hydroxide concentration of about 1.5% (wt. basis, i.e. about 0.37N or about a 67:1 molar ratio of alcohol:alkali) in alcohol. Virtually the same degree of transesterification occurs at lower alkali concentrations (e.g., down to approximately 0.1N), and contaminating free fatty acid levels are reduced. At alkali concentrations of approximately 0.05N and below, transesterification is less efficient and triglycerides are also found in the product mixture.

When conducted using the reactor geometry and reactants described herein, consisting of feedstock (e.g., flaked soybeans), alcohol (e.g., methanol) and alkali shaken in a sealed container, generally about 0.04-about 25 ml (e.g., 0.04-25 ml) of alcohol per gram of lipid source (e.g., oilseed) are utilized (preferably about 0.1-about 10 ml (e.g., 0.1-10 ml) of alcohol, more preferably about 0.5-4 ml (e.g., 0.5-4 ml) of alcohol). This corresponds to molar proportions of alcohol to lipid source (e.g., oilseed) triglyceride of 3.38-2178:1, 8.71-871:1, and 43.6-326:1 respectively.

The amounts of alcohol necessary, in the context of reaction stoichiometry, to achieve full esterification are quite small. For example, the volume of methanol theoretically necessary and sufficient to completely transesterify the triglycerides in 1 gm of soybean with an oil content of 25% is only 0.035 ml. Larger volumes are specified above due largely to the fact that the flaked lipid source (e.g., oilseed) substrate matrix both binds and passively retains a certain amount of the alkaline alcohol solution. The excess alcohol may also facilitate access of the reaction catalyst (methoxide) to the locations of lipid, within the matrix of the substrate, or allow the reaction to occur in the presence of water present in the feedstock. The disadvantage of the use of substantially larger than stochiometric amounts of alcohol is the effort, difficulty and expense of removing unreacted alcohol from the fatty acid ester product at the end of the reaction.

The specifications above are driven not solely by the chemical requirements of the system, but also by the reaction geometry employed. Variations in reactor design that impact such parameters as the amount of alkaline alcohol required to sufficiently expose all lipid in the lipid source (e.g., oilseed) to that reactant solution will impact the amount of alkaline alcohol that is optimum for maximum ester production. Alternate reaction geometries, such as but not limited to trickle-through extraction devices that pass the alkaline alcohol solution over the lipid source (e.g., oilseed) multiple times, can be imagined that might perform optimally with greater or lesser amounts of alkaline alcohol. The specifications listed above are not intended to eliminate the possibility that such other optima might exist for other reaction geometries.

At a reactant ratio of 5:0.37:0.0055 (gm flaked seed:mole alcohol:mole alkali), the removal of triglyceride from the substrate, in the case of soybeans, is virtually complete (98% as measured by Soxhlet extraction of post-transesterification flakes) within one hour of reaction at 60° C., and fatty acid ester synthesis is substantial.

To prevent evaporation of the alcohol reactant, the reactions are conducted in sealed containers in a preferred embodiment of the invention. No further added pressure need be applied in order to achieve transesterification, though the reaction may proceed at increased pressures. Generally, the method is conducted at atmospheric pressure.

The reaction proceeds well at room temperature (e.g., about 22° C.). Higher reaction temperatures increase the rate of transesterification and yield more fatty acid ester. Above about 65° C., extra containment procedures may be necessary due to elevated pressures. Such higher temperatures and pressures are not necessary to obtain significant amounts of transesterification. As the reaction temperature is reduced toward normal room temperature (22° C.) the amount of free fatty acid liberated during the reaction is reduced. Each individual substrate requires an examination to determine the temperature(s) giving maximum transesterification in an acceptable period of reaction time. Similarly the ratio of alcohol and catalyst to one another and to the mass of feedstock, in order to obtain maximal transesterification, may vary from feedstock to feedstock and temperature to temperature. Reaction conditions for maximum transesterification can be determined by experiments similar to those described below. Generally, and surprisingly, the methods described herein are capable of conversion of at least about 75% (e.g., at least 75%), preferably at least about 80% (e.g., at least 80%), preferably at least about 85% (e.g., at least 85%), preferably at least about 90% (e.g., at least 90%), preferably at least about 95% (e.g., at least 95%), preferably at least about 96% (e.g., at least 96%), preferably at least about 97% (e.g., at least 97%), preferably at least about 98% (e.g., at least 98%), preferably at least about 99% (e.g., at least 99%) or greater of the lipids in the feedstock into simple alkyl esters; most preferably about 100% (e.g., 100%).

Generally, about 0.04-about 25 ml (e.g., 0.04-25 ml) of alcohol per gram of feedstock are utilized (preferably about 0.1-about 10 (e.g., 0.1-10 ml) of alcohol, more preferably about 0.5-about 4 ml (e.g., 0.5-4 ml) of alcohol). Generally, about 0.02-about 0.4 molar (e.g., 0.02-0.4 molar) of alkali in the alcohol (preferably about 0.06-about 0.13 molar (e.g., 0.06-0.13 molar) of alkali are utilized, more preferably about 0.08-about 0.11 molar (e.g., 0.08-0.11 molar) of alkali).

Generally, the reaction time is usually about 1-about 12 hours (e.g., 1-12 hours), preferably about 8-about 9.5 hours (e.g., 8-9.5 hours), more preferably about 7-about 9 hours (e.g., 7-9 hours). Generally, the reaction temperature is usually about 20°-about 70° C. (e.g., 20°-70° C.), preferably about 20°-about 40° C. (e.g., 20°-40° C.), more preferably about 20°-about 30° C. (e.g., 20°-30° C.). Preferably, the reaction time is about 8 hours (e.g., 8 hours) at about 23° C. (e.g, 23° C.) or about 6 hours (e.g., 6 hours) at about 60° C. (e.g., 60° C.).

The fatty acid alkyl ester product will typically contain less than about 1000 mg FFA (free fatty acids)/g fatty acid alkyl esters; the fatty acid alkyl ester product may contain less than about 800 mg FFA/g fatty acid alkyl esters, less than about 400 mg FFA/g fatty acid alkyl esters, less than about 200 mg FFA/g fatty acid alkyl esters, or less than about 50 mg FFA/g fatty acid alkyl esters. As noted above, production of FFA is reduced when the reaction is conducted at lower temperatures or greater ratios of alcohol to alkali. Generally, the fatty acid alkyl ester product will contain less than about 5% weight basis of unreacted triacylglycerols, unreacted diacylglycerides, and unreacted monoacylglycerides, preferably less than about 1% weight basis of unreacted triacylglycerols, unreacted diacylglycerides, and unreacted monoacylglycerides. The identity of the fatty acid alkyl ester product is determined by the identities of the alcohol and the oil source employed in the reaction. Preferably, in the context of a fuel for compression ignition engines, the fatty acid alkyl ester product is fatty acid ethyl esters or more preferably fatty acid methyl esters.

The following examples are intended only to further illustrate the invention and are not intended to limit the scope of the invention as defined by the claims.

EXAMPLE 1

Soy bean flakes, produced from soybeans that had been treated at 150° F. for about one minute, the item used industrially in the hexane-extraction based recovery of soybean oil, were obtained from a commercial edible oil extraction facility.

Experiment I: 5 g flaked soybeans were added to two approximately 150 ml screw capped glass bottles as reactors. To one glass bottle was added 15 ml of methyl alcohol in which 0.22 gm of sodium hydroxide had been dissolved. To the other was added 15 ml of isopropyl alcohol containing 0.22 gm sodium hydroxide. The bottles were capped and swirled at 60° C., after 2 hours 0.5 ml was removed and frozen at −20° C. for later analysis. After 17.5 hr., the liquid was removed from atop the flaked beans. The content of the 2 and 17.5 h samples were analyzed by thin layer chromatography (TLC) of 10 microliter samples on silica gel with standards (i.e., soybean tri-, di-, and mono-acylglycerols, free fatty acids, and fatty acid methyl esters). The developing solvent was hexane/diethyl ether/acetic acid (80/20/1, v/v/v). After the run, the plate was air dried, sprayed with concentrated sulfuric acid, and heated to display the locations of carbonaceous compounds.

The results are shown in FIG. 1 (counting lanes from the left in the Figure):
Lane 1: standard (known soybean fatty acid methyl ester)
Lane 2: standard (known soybean triglycerides)
Lane 3: standard (1,3-diacylglycerol)
Lane 4: standard (1-monoacylglycerol)
Lane 5: standard (soybean free fatty acids)
Lane 6: transesterification attempt, alcohol=isopropyl, 2 hr. reaction.
Lane 7: transesterification attempt, alcohol=methyl, 2 hr. reaction
Lane 8: transesterification attempt, alcohol=isopropyl, 17.5 hr
Lane 9: transesterification attempt alcohol=methyl, 17.5 hr Interpretation of FIG. 1: Fatty acid ester was present, predominant in all reactions, in tubes 6-8. Of alcohols tested, methanol was superior to isopropanol in yield of ester. Substantial amounts of free fatty acids were present in all reactions. Except at extended reaction time with isopropanol, no triglyceride was present in the extracts. Diacylglycerol and monoacylglycerol were present in all reactions, lanes 6-8. Thus in situ transesterification was demonstrated to produce fatty acid esters. Ample free fatty acids were also produced which suggested that triglyceride hydrolysis occurred.

Experiment II: The physical setup was the same as Experiment I, except that the bean flakes were dried under vacuum to a constant weight prior to use, in an attempt to remove water that might be the cause of the free fatty acid production noted above. Alcohols tested were methanol, methanol dried with sodium sulfate (which, without being bound by theory, supposedly reduces water content and reduces generation of free fatty acids), and isopropanol. Also conducted was a reaction containing methanol but no sodium hydroxide to test whether the latter was required to achieve esterification. Incubation times: 1 and 16.25 h. Analysis by TLC as in Experiment I.

Figure 2:
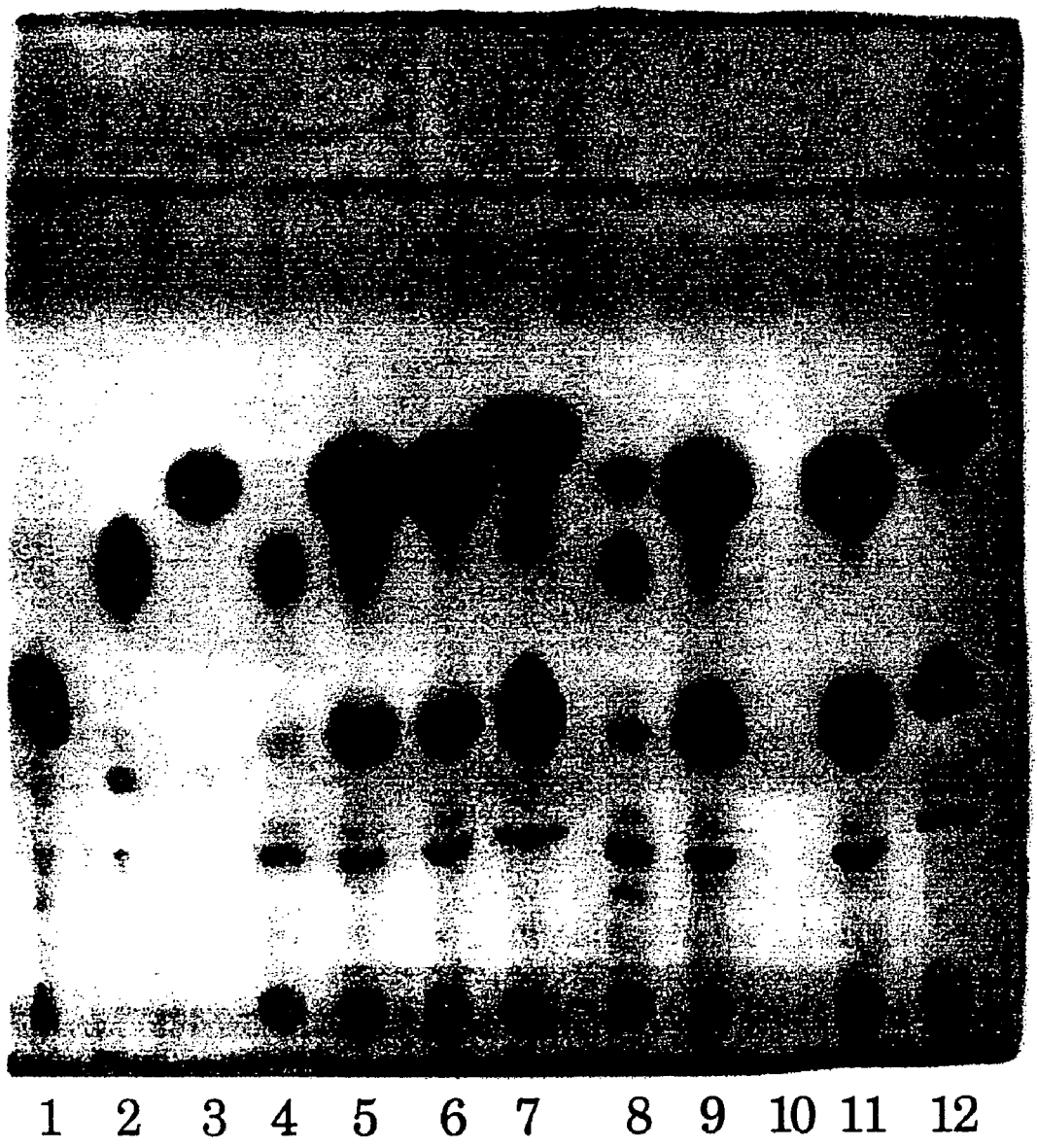

The results are shown in FIG. 2 (counting lanes from the left in the Figure):
Lane 1: standard (soybean free fatty acid)
Lane 2: standard (soybean triglycerides)
Lane 3: standard (soybean fatty acid methyl ester)
Lane 4: methanol, no sodium hydroxide, 1 hr. reaction
Lane 5: methanol plus base, 1 hr.
Lane 6: dry methanol plus base, 1 hr.
Lane 7: isopropanol plus base, 1 hr.
Lane 8: methanol alone, 16.25 hr.
Lane 9: same as 5, 16.25 h.
Lane 10: blank
Lane 11: same as 6, 16.25 hours
Lane 12: same as 7, 16.25 hours Interpretation of FIG. 2: Fatty acid ester was not made in the absence of sodium hydroxide in 1 hr. Some may have been made over the course of 16.25 hr. reaction. Some triglyceride was extracted by methanol without base. Ester was produced in 1 hr reactions and was predominant species present. The longer reaction time appeared to produce no greater ester yield. Free fatty acid was produced in all reactions containing alcohol and base. Drying the beans and the alcohol did not retard free fatty acid production. Again, both methanol and isopropanol were able to achieve strong ester production. Amount of ester was roughly the same with either.

Experiment III: Physical setup was same as Experiment I. In some tubes dry bean flakes were the substrate, in others the flakes were used as received, again to investigate the theory that water might be the cause of the free fatty acids being produced. Alcohols tested were methanol, ethanol, and ethanol dried with sodium sulfate (which, without being bound by theory, supposedly reduces water content and reduces generation of free fatty acids). All reactions contained sodium hydroxide. Incubation times: 1 and 16.5 h. Analysis by TLC as in Experiment I.

Figure 3:
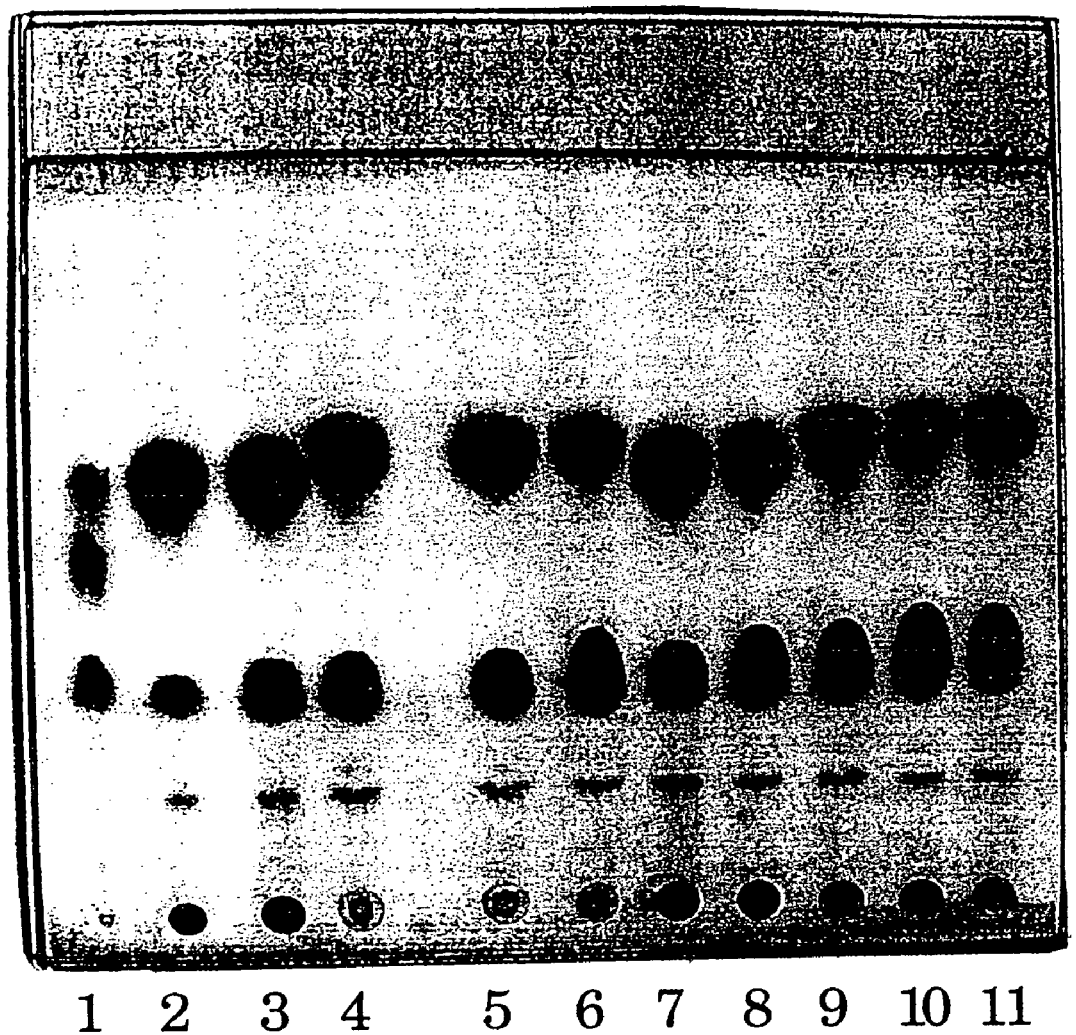

The results are shown in FIG. 3 (counting lanes from the left in the Figure):
Lane 1: standards (mix containing FFA, triglyceride, methyl ester)
Lane 2: methanol, dry flakes, 1 hr.
Lane 3: methanol, flakes as received, 1 hr.
Lane 4: ethanol, dry flakes, 1 hr.
Lane 5: ethanol, flakes as received, 1 hr.
Lane 6: dry ethanol, dry flakes, 1 hr.
Lane 7: same as 2, 16.5 h
Lane 8: same as 3, 16.5 hr.
Lane 9: same as 4, 16.5 h.
Lane 10: same as 5, 16.5 hr.
Lane 11: same as 6, 16.25 hr.

Interpretation of FIG. 3: Fatty acid ester was made in substantial amounts under all circumstances (i.e., ethanol also was an acceptable alcohol). One hour incubations were sufficient, 16.5 hr may yield no additional ester product. Predominant production of free fatty acid occurred. Removal of water from reactants reduced this little if at all. As previously seen, minor amounts of di- and perhaps mono-acylglycerols were present.

Experiment IV: The 'Soxhlet extractor' is a standard device used to extract solvent-soluble components from a material. It repeatedly passes a batch of solvent over a charge of material, successively extracting a higher and higher proportion of soluble materials. The present experiment investigated the ability of such an approach to achieve transesterification of the fatty acids in soybeans.

The extraction chamber of a Soxhlet extractor was charged with 15 gm of soybean flakes. To the liquid chamber was added 100 mL of ethanol and sodium hydroxide to 1%. Heat was applied to boil the ethanol solution, which was condensed and allowed to drip onto the flakes. Extraction was continued for either 1.75 or 5.5 hr. To examine the effect of trace water content, the reactions were conducted (1) using ethanol and soy flakes as received, and (2) with soy flakes that had been dried by lyophilization and ethanol dried by sodium sulfate pretreatment.

Thin layer chromatography was conducted as above to analyze for formation of ester.

The results are shown in FIG. 3 (counting lanes from the left in the Figure; Note: ethanol throughout):
Lane 1: standards (mix containing, FFA, triglyceride, methyl ester)
Lane 2: 5 uL, dry reaction, 1.75 hr incubation.

Lane 3: 15 uL, dry reaction, 1.75 hr incubation
Lane 4: 5 uL, not dried, 1.75 hr.
Lane 5: 15 uL, not dried, 1.75 hr.
Lane 6: same as #2, but 5.5 hr. incubation
Lane 7: same as #3, but 5.5 hr.
Lane 8: same as #4, but 5.5 hr.
Lane 9: same as #5, but 5.5 hr.

Figure 4:
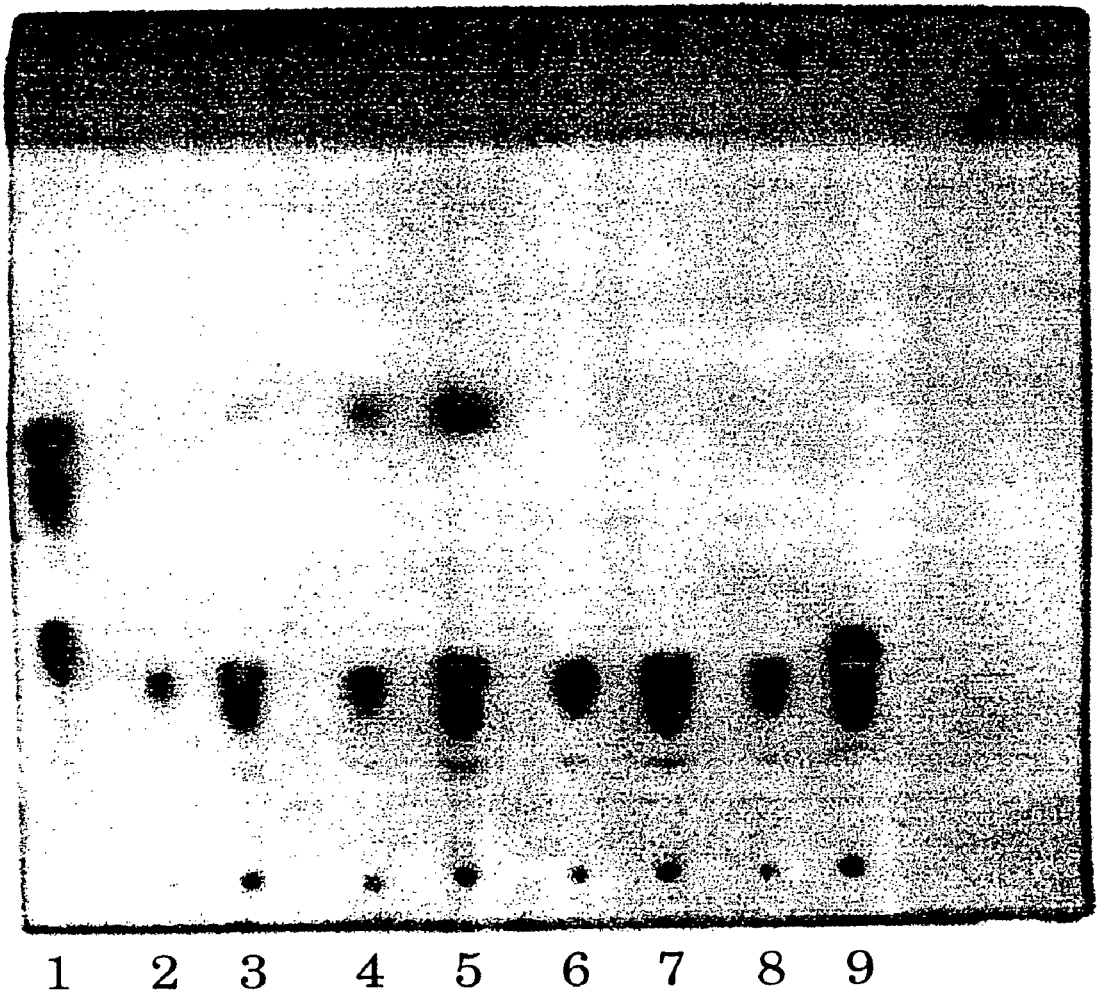
Figure 5:
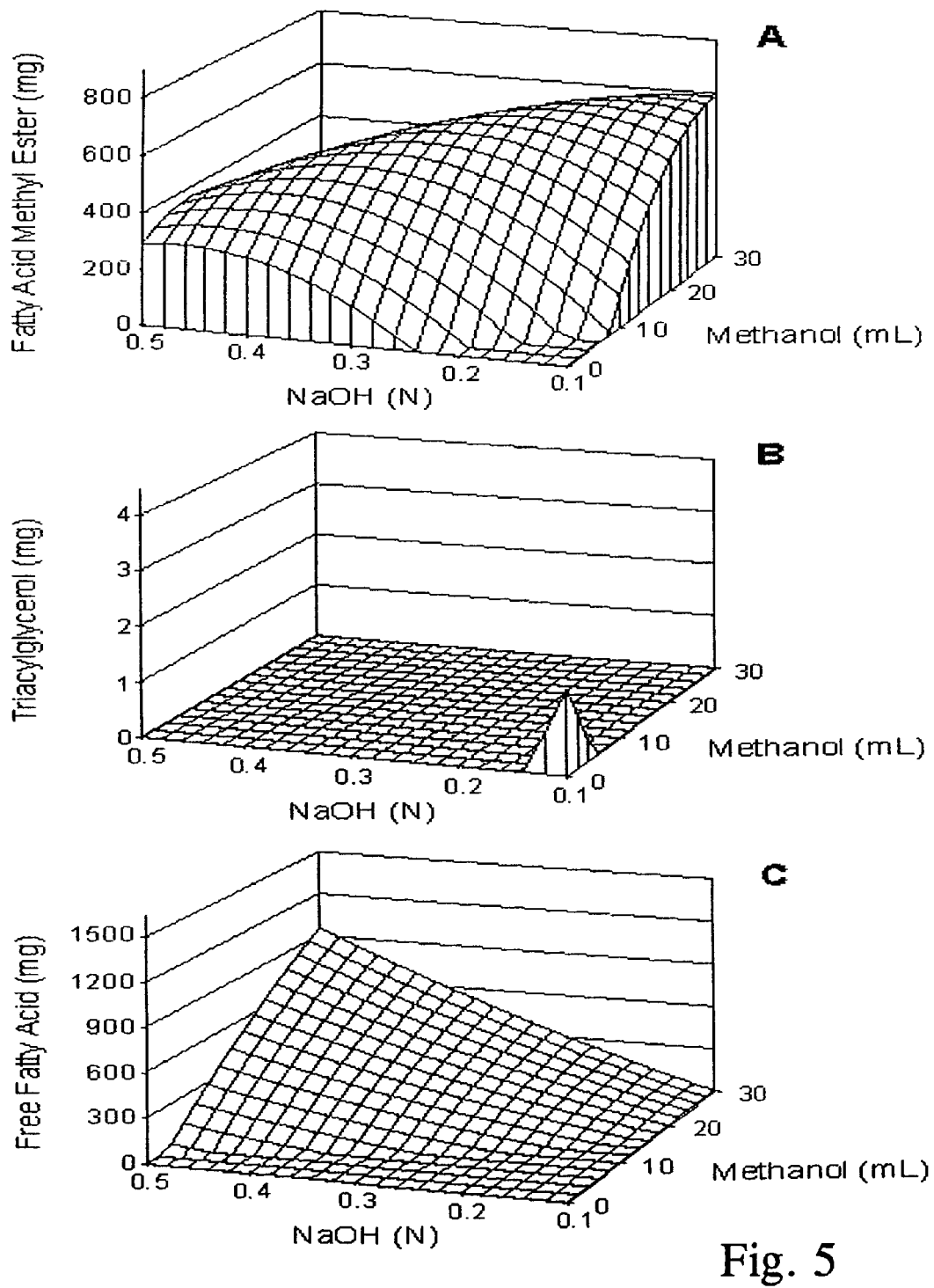
FIG. 5 shows predicted response surfaces, calculated from Eqn. 1-3 below, for the product composition after 2 hours of in situ transesterification of 5.00 g of soy flakes at 60° C., as a function of the amount of alcohol and the concentration of sodium hydroxide; (A) FAME; (B) TAG; (C) FFA.

Interpretation of FIG. 4: TLC gave evidence of fatty acid ester production with esters being present after 1.75 hr. incubation. Largest ester spot was obtained in reaction using undried reagents (lane 5). Absence of esters at 5.5 hr suggested destruction of those formed at earlier incubation times during incubations of extended duration, a hypothesis consistent with the free fatty acids present both after 1.75 hr but more so at 5.5 hr. There may have been monoglycerides present in material lingering at origin on TLC plates. It must be born in mind that the liquid phase volume in this reaction was 125 mL, whereas in experiment I-III it was just 15 mL. Thus, the fact that the ester spot was fainter in this experiment may not necessarily mean that transesterification was weaker with the Soxhlet approach; it may just be due to the greater dilution of the ester.

The disclosed method eliminates the costs of oil extraction and refining in the production of fatty acid alkyl esters. These costs constitute roughly 60% of the cost of refined oil, which itself accounts for roughly 75% of the cost of biodiesel production. Thus, it is calculated that elimination of extraction and refining could reduce the cost of biodiesel production by approximately 45%. Production costs are approximately $2.20/gal when the feedstock is refined oil. A 45% decrease in feedstock cost would reduce this overall production cost to $1.21/gal. With annual sales volumes of 20 million gallons, this amounts to a savings of approximately $14 million in production costs if all that biodiesel were originally made from refined oil (as much, but not all, is). It is likely that a method offering such a reduction in cost would be adopted by a large proportion of producers and could be sufficient to assure the economic competitiveness of biodiesel.

Although simple batch methods have been tried to date, the development of a continuous process can be readily envisioned by one skilled in the art.

EXAMPLE 2

Chemicals: Flaked soybeans, prepared for hexane extraction in a commercial oil plant, had a thickness of 0.28 to 0.35 mm. The oil content of the flakes, determined by extraction with hexane for 4.5 h in a Soxhlet apparatus, was 23.9% (mass basis). Their moisture content, determined by overnight lyophilization, was 7.4% (mass basis). These values are typical for the oil and water contents of commercial flakes soybeans (Williams, M. A., and R. J. Hron, Sr., Obtaining Oils and Fats from Source Materials, in Bailey's Industrial Oil & Fat Products, Fifth Edn., Vol. 4, edited by Y. H. Hui, John Wiley & Sons, Inc. New York, pp. 61-155). Flakes were stored under nitrogen at −20° C.

Lipid standards were obtained from Sigma-Aldrich. Palmitic, stearic, oleic, linoleic, and linolenic acids mixed in amounts proportional to their mass abundance in soybean oil (Fritz, E., and R. W. Johnson, Raw Materials for Fatty Acids, in Fatty Acids in Industry, Processes, Properties, Derivatives, Applications, edited by R. W. Johnson, and E. Fritz, Marcel Dekker, New York, 1989, pp. 1-20.) served as the FFA standard. A mixture of FAME whose composition reflected the fatty acid content of soy oil (RM-1) was the product of Matreya, Inc. (Pleasant Gap, Pa.). Necessary reagents for the determination of glycerol were obtained as components of a triglyceride assay kit (Sigma-Aldrich). Organic solvents were B&J Brand™ High Purity Grade (Burdick & Jackson, Inc., Muskegon, Mich.). Sulfuric acid (96.3%) was the product of Mallinckrodt Baker (Paris, Ky.). Other reagents were Analytical Reagent grade quality or better.

Conduct and optimization of in situ transesterification: Flaked soybeans (5.00 g unless otherwise stated) were mixed with alkaline alcohol (an alcohol, in this case methanol, in which alkali, in this case sodium hydroxide, is dissolved) in screw-capped bottles of capacity at least 5 times the reaction volume. These were mixed by orbital shaking at a speed sufficient to keep the flakes well suspended. Following reaction, bottles were allowed to sit for 15 min at room temperature to allow the flakes to settle and the reaction to cool. The liquid phase was removed and, for qualitative analysis, directly analyzed by TLC. For quantitative analysis the spent flakes were washed twice by resuspension in 10 mL methanol and the washes were pooled with the reaction liquid. The combined methanol layers were centrifuged (15 min, 5900× g) and the resulting supernatant removed. Following its dilution to 40 mL with methanol, 1 mL was mixed with 10 mL of 2M KCl—HCl buffer, pH 1.0, and extracted with 10 mL hexane. The organic layer was recovered and its lipid components analyzed by HPLC.

Focusing on the reaction with methanol, Central Composite Response Surface design methods (Box, G.E.P., W. G. Hunter, and J. S. Hunter, Statistics for Experimenters, Wiley, New York 1978) were employed to coordinately investigate the effects and interactions of the amount of alkaline methanol, its NaOH concentration, and reaction time on the yields of FAME, FFA and unreacted acylglycerols (AG) in the liquid phase. Preliminary studies (data not shown) were conducted to focus the statistically designed work in the region of variable space giving the highest FAME production.

Two temperatures were investigated: 60° C. and 23° C. (room temperature). For the 60° C. reaction, the amounts of alkaline methanol tested were 7.5 (the minimum to cover 5 g of flakes), 12.1, 18.7, 25.4 and 30.0 mL; the NaOH concentrations tested were 0.05, 0.14, 0.275, 0.41 and 0.5 N, and reaction times were 0.25, 1.8, 4.00, 6.2 and 7.8 h. For reactions at room temperature, the amounts of alkaline methanol tested were 14.2, 18.7, 25.4, 32.1 and 36.7 mL; NaOH concentrations were 0.02, 0.052, 0.10, 0.148 and 0.18 N; and reaction times were 2.5, 4.0, 6.2, 8.5 and 10.0 h. Each experimental series involved 20 reactions at various combinations of these levels.

FAME, FFA and AG levels were quantitated by HPLC following sample preparation as previously described in this section. Best-fit equations correlating this data with the composition of the reactions were constructed using SAS/STAT software (SAS/STAT User's Guide, Version 8, SAS Institute Inc., Cary, N.C., 1999). Numerical analysis of these equations and examination of the corresponding three dimensional surfaces allowed identification of the conditions predicted to give maximum FAME yield with minimum contaminating FFA and AG.

Determination of transesterification efficiency (room temperature): Samples (100 g, conducted in duplicate) of soy flakes were subjected to in situ transesterification at room temperature under identified optimal reaction conditions (680 mL of 0.1 N NaOH in methanol, 7.75 h incubation). After cooling and settling of the flakes the liquid phase was recovered by filtration. The flakes were washed three times by resuspension in 150 mL methanol for 10 min each, and the washes pooled with the reaction liquid. The extracted flakes were air-dried, lyophilized to dryness, and their mass determined.

To determine the efficiency of lipid removal from the flakes during in situ transesterification, 20.0 g of the dried, post-reaction flakes was extracted for 4 h with 150 mL hexane in a Soxhlet apparatus. The liquid phase was recovered, its hexane removed under vacuum, and the acylglycerol content of the extract was determined by HPLC.

The transesterification reaction liquid phase and the liquid from the post-transesterification washes of the flakes were pooled, adjusted to pH 3 with concentrated HCl, and the methanol removed under vacuum. The resulting syrup was resuspended in 150 mL water and extracted 5 times with 300 mL of hexane. The pooled organic phases were dried over sodium sulfate, recovered, and their hexane removed under vacuum. The mass of the resulting liquid was determined, and its FAME and FFA contents measured by HPLC.

Determination of fate of glycerol: Samples (28-30 g, conducted in duplicate) of the dried post-transesterification flakes generated in the preceding section were washed by swirling for 30 min. each in 2×300 mL water. The washes were recovered by filtration, pooled, adjusted to neutrality with HCl, and the glycerol content was determined.

Glycerol contents of this spent-flake wash, and of the water-soluble portion of the original reaction liquid, prepared as described in the preceding section, were determined by an enzymatic assay linking the glycerol kinase-catalyzed phosphorylation of glycerol, via the intermediate actions of pyruvate kinase and lactate dyhydrogenase, to the oxidation of NADH (Instruction Manual, Triglycerides Determination Kit, Sigma-Aldrich, St. Louis, Procedure No. 320-UA, 1996). Solutions of glycerol of known concentration served as reference standards.

Thin layer chromatography: TLC was performed on 250 μm Silica G plates (Analtech, Newark, Del.). The developing solvent was hexane:diethylether:acetic acid (80:20:1, volume basis). Spots were visualized by spraying with sulfuric acid and charring on a hotplate.

High performance liquid chromatography: The presence and amounts of FAME, FFA and AGs were determined by HPLC on a silica column (Haas, M. J., and K. M. Scott, J. Am. Oil Chem. Soc., 73:1393-1401 (1996)). Peaks were eluted with gradients of isopropanol and water in hexane-0.6% acetic acid (v/v), detected by evaporative light scattering, and quantitated by reference to standard curves constructed with known pure compounds. Minimum detectable levels of lipid species per reaction conducted as described above ("Conduct and optimization of in situ transesterification") were: FAME: 60 mg; FFA: 1.1 mg; triacylglycerols, diacylglycerols (DAG), monoacylglycerols (MAG): 1.8 μg; phosphoacylglycerols: 2.7 μg.

Results and Discussion: Preliminary investigations demonstrated that even brief incubations of soy flakes in alkaline solutions of simple alcohols at 60° C. resulted in the production of fatty acid alkyl esters. This occurred with methanol, ethanol and isopropanol, suggesting that the effect was a general one. Under alkaline conditions, ester production with methanol appeared as strong as with less polar alcohols. FFA were produced during alkaline in situ transesterification.

Optimization of reaction: Optimization of reaction conditions has the potential to reduce reagent consumption, increase yields and decrease contamination by FFA and AG. Due to the industrial importance of the methyl esters of fatty acids, we focused on optimizing conditions for in situ transesterification with this alcohol though it is expected that similar results will occur with other alcohols.

Two reaction temperatures were investigated: (1) 60° C., which is sufficiently warm to achieve rapid reaction, yet is below the boiling point of the system, eliminating the need for pressurized equipment, and (2) 23° C. (room temp.), at which heating of the reaction is not required and at which the reduced volatility of the alcohol component eases vapor containment and reduces the need for solvent replacement. Reaction conditions yielding high degrees of transesterification with low levels of FFA and free AG were sought. A low content of FFA is desirable because these represent lost potential FAME. Also, low FFA levels are specified for FAME preparations intended for use as biodiesel (Standard Specification for Biodiesel Fuel (B100) Blend Stock for Distillate Fuels, Designation D 6751-02, American Society for Testing and Materials, West Conshohocken, Pa. (2002)), which necessitates additional cleanup steps for high-FFA preparations.

The best-fit second-order response surfaces to describe the production of FAME, FFA and TAG in reactions conducted at 60° C. are given by Eqn. 1-3:

$$FAME = -1280 + 138T + 93.7V + 6160B - 0.464T^2 - 2.89TV - 275TB - 1.26V^2 - 137VB + 6010B^2 \quad (1)$$

$$FFA = -184 + 34.4T + 5.16V + 771B - 8.22T^2 + 2.02TV + 96.2TB - 0.347V^2 + 75.8VB + 1140B^2 \quad (2)$$

$$TAG = 4.62 + 0.956T + 0.253V - 54.2B - 0.0661T^2 - 0.0117TV - 0.587TB - 0.00735V^2 + 0.196VB + 78.4B^2 \quad (3)$$

where FAME, FFA and TAG are expressed as mg/reaction, T=incubation time (hours), V=volume of alkaline alcohol (mL), and B=alkali concentration (Normality) in the alcohol. These equations gave acceptable fits to the experimental data, with $R^2$ values of 86.4% for FAME, 97.5% for FFA, and 64.0% for TAG. Di-, mono- and phospho-AGs were not detected in FAME samples prepared at 60° C.

Figure 6:
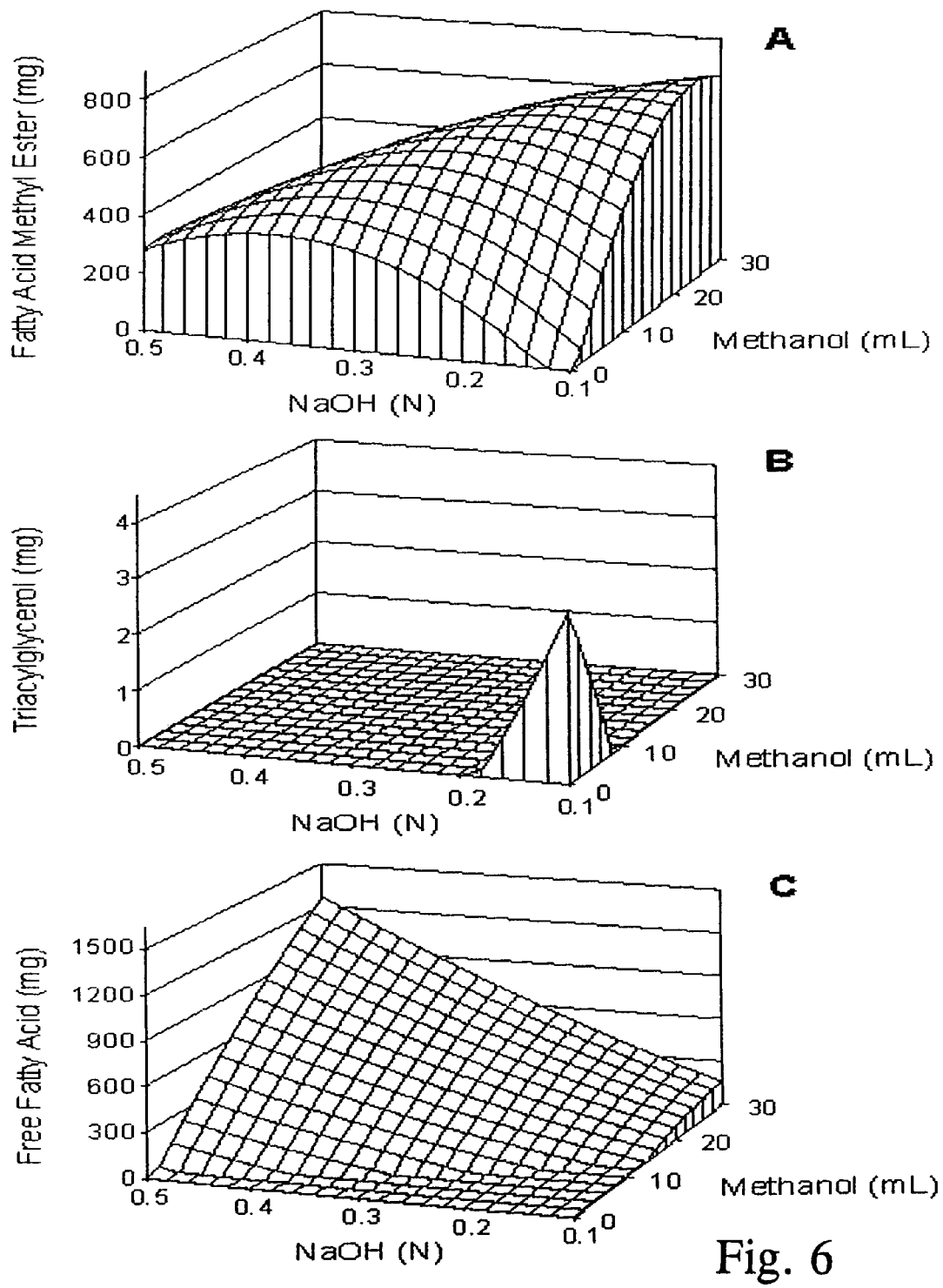
FIG. 6 shows predicted response surfaces, calculated from Eqn. 1-3 below, for the product composition after 6 hours in situ transesterification of 5.00 g of soy flakes at 60° C., as a function of the amount of alcohol and the concentration of sodium hydroxide; (A) FAME; (B) TAG; (C) FFA.
Figure 7:
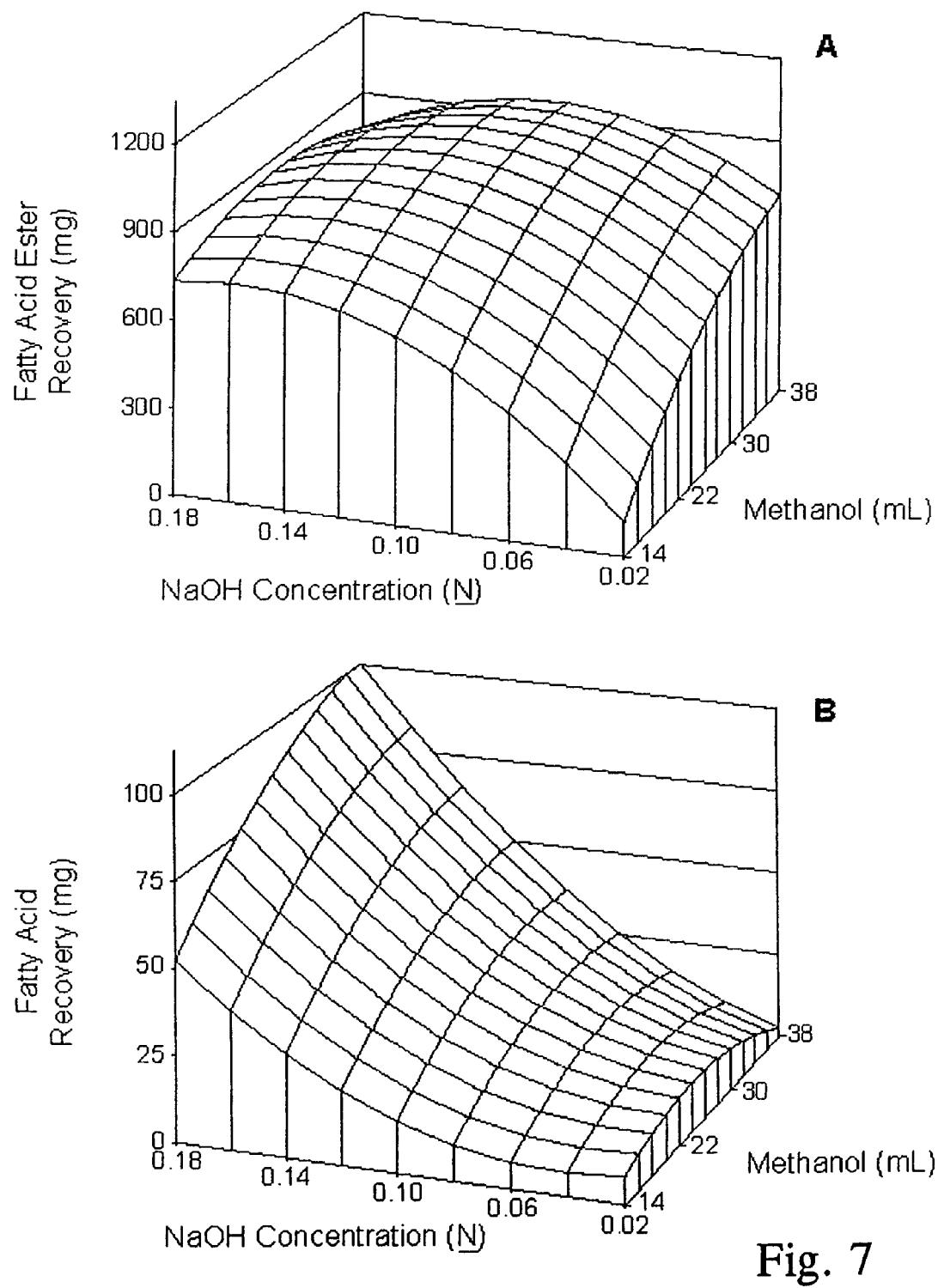
FIG. 7 shows predicted response surfaces, calculated from Eqn. 3 and 4 below, for the product composition after 8 h of in situ transesterification of 5.00 g soy flakes at 23° C., as a function of the amount of alcohol and the concentration of sodium hydroxide; (A) FAME; (B) FFA.

Eqn. 1-3 allowed construction of surfaces describing the levels of TAG, FAME, and FFA in the reaction liquid as a function of its composition during in situ transesterification at 60° C. (FIGS. 6 and 7). After two hours, FAME production was nearly complete; additional incubation, to 6 hr total, only slightly increased the yield. In fact, transesterification proceeded rapidly, with some reactions surprisingly producing 80% of the FAME yield seen at 6 h. within 15 min. Incubation beyond 6 h did not further increase yield. The level of unreacted oilseed TAG, extracted from the seeds but not transesterified, was low over virtually the entire coordinate space examined (FIGS. 6 and 7). FFA levels were also low in reactions containing low alkali concentrations and low to moderate amounts of alcohol (FIGS. 6 and 7). Numerical optimization, and examination of FIGS. 6 and 7, indicated that at 60° C. the conditions resulting in high FAME production with low contamination by FFA and TAG from 5 gm soy flakes were 12 to 25 mL methanol, an NaOH concentration between 0.1 and 0.2 N, and a reaction time of approximately 6 h. The greater the alcohol volume the lower the alkali concentration required to give good yields of FAME with low FFA and AG contamination. Using 22.5 mL of 0.1 N NaOH the predicted amounts of FAME, FFA and TAG were 762, 62 and 3 mg, respectively. Upon reducing the methanol to 12.5 mL and increasing NaOH to 0.18 N the predicted product composition after 7.7 h reaction was 675 mg FAME, less than 1 mg FFA, and no TAG. These latter conditions correspond to a molar ratio of 226:1:1.6 for methanol:TAG:alkali. By comparison, optimal conditions for the conventional alkali-catalyzed transesterification of refined soy oil at 60° C. are molar ratios of 6:1:0.22 for methanol:TAG:NaOH (11). Thus, in the present configuration the in situ method employs about 38 times more alcohol and 7 times more alkali than does the conventional method. The excess reagents could be recovered for reuse if desired.

When conducted at room temperature, no tri-, di-, mono- or phospho-AGs were detected in the liquid phase following transesterification. The best-fit second-order response surfaces to describe the FAME and FFA levels as a function of the composition of the reaction were:

$$FAME=-1355+129.2T+63.22V+13710B-8.214T^2- \\ 0.2204TV-147.0TB-0.7243V^2-143.8VB- \\ 33360B^2 \quad (4)$$

$$FFA=-21.78-9.141T+2.050V-733.0B-1.005T^2+ \\ 0.0570TV+41.72TB-0.0580V^2+14.22VB+2393B^2 \quad (5)$$

The $R^2$ values for the fits of these equations to the data were 93.7% for FAME and 98.6% for FFA, indicating that the data were well modeled by the equations.

Using Eqn. 4 and 5, predictive surfaces were constructed to describe the composition of the reaction products as a function of alkali concentration, amount of methanol, and reaction time at room temperature (FIG. 8). Examination of the surfaces in FIG. 8 makes it clear that reaction conditions can be identified such that any desired degree of transesterification of the lipid in the feedstock is achieved. Thus, for example, one could choose a combination of reaction time, and amounts of alcohol, alkali, and lipid bearing material to achieve conversion of any percentage of the lipid in the feedstock to ester. In the context of producing fatty acid esters for use as biodiesel, high levels of conversion of lipid to simple fatty acid ester are most efficient and economical. Thus it will be appreciated that the approach described herein is capable of identifying conditions capable of achieving, as noted above, very high conversion of the lipids in the feedstock into simple alkyl esters. Given the conditions described in this example, maximum FAME production was achieved after about 8 h of reaction, with surprisingly 90% of maximum occurring by 2 h (data not shown). For reactions of about 8 h duration, the best yields of FAME and lowest levels of contamination by FFA were predicted for reactions containing 5 gm flakes and 30 mL or more of methanol (minimum molar ratio of methanol:triglyceride=543) with an NaOH concentration of 0.09 N (molar ratio of NaOH: triglyceride=2.0). Predicted FAME and FFA levels under these conditions were on the order of 940 and 35 mg, respectively. This is a higher FAME yield and lower FFA level than predicted for reactions under optimal conditions at 60° C. As at 60° C., the molar reagent requirements at room temperature are substantially greater than those for alkaline transesterification of refined oil (11): 90 times more methanol and 9 times more NaOH. The methanol requirement at room temperature was also approximately 2.4 times that at 60° C. (above), but the additional expense of this increase may be compensated for by the reduced costs of room temperature operation.

Transesterification efficiency: The FAME fraction recovered after in situ transesterification of 100 g of soy flakes at room temperature for 7.75 h under optimal conditions (680 mL of 0.1N NaOH in methanol) weighed 19.5 g and was determined by HPLC to contain 18.9 g (97 wt %) FAME and 0.14 g (0.72 wt %) FFA (all data are means of replicate reactions; individual values differed from the means by no more than 4%). Given an initial lipid content of 22.1% in the flakes, the theoretical maximum FAME recovery was 20.4 gm. Overall FAME recovery was thus surprisingly 92.6% of theoretical. No acylglycerols were detected in the FAME product.

Soy flakes lost 31.9% of their mass during in situ transesterification at room temperature. This exceeds the total lipid content of the flakes (22.1%) but is consistent with a high degree of removal of water (original content: 7.4%) as well as lipid during transesterification. Hexane extraction of dried post-transesterification flakes removed 1.3 g of material. HPLC analysis indicated that triacylglycerols made up 83% of this material. Thus, approximately 1.1 g, 5% of the lipid content of the flakes, was neither extracted nor transesterified during the in situ reaction. This would contribute to the less than quantitative recovery of FAME that was observed.

Using acidic methanol under reflux, Kildiran et al. (J. Am. Oil Chem. Soc., 73: 225-228 (1996)) observed a maximum extraction of 40% of the oil from finely ground soy beans, with only 55% transesterification of this extracted oil, giving an overall FAME yield of 22%. As opposed to acid catalysis, the alkaline room temperature reaction conducted herein surprisingly achieved a much greater removal of oil from the substrate (95%) and more effective transesterification of the extracted oil (98%). Some of the unrecovered lipid and ester may have been lost to a small emulsion layer that formed during extraction of the samples with water and hexane during analysis.

Fate of glycerol: Glycerol is a coproduct of the transesterification process. There was interest in determining the fate of glycerol in the in situ process, since current biodiesel specifications (Standard Specification for Biodiesel Fuel (B100) Blend Stock for Distillate Fuels, Designation D 6751-02, American Society for Testing and Materials, West Conshohocken, Pa. (2002)) limit the amount allowed, and since its recovery could give rise to another product stream. Also, since a typical use of solvent-extracted oilseed flakes is as an animal feed, there was interest in determining the degree to which glycerol might be bound to the flake fraction, where it might affect nutritional performance of the flakes.

Aqueous extraction was used to recover glycerol from the FAME and the spent-flake fractions of the 100 g reactions described above. Enzymatic assay determined that recovered glycerol was located predominantly (93%) in the liquid fraction following transesterification: its contents in the FAME and spent-flake fractions were 1.9 and 0.14 g, respectively. The sum of these values accounts for approximately 94% of maximum theoretical glycerol recovery. Some of the remainder can be attributed to the 5% of the oil fraction that was not extracted from the flakes.

(1) The moisture content of the feedstock effects the amounts of reagents required to achieve high degrees of transesterification. Thus whereas a ratio of alcohol:triglyceride of 543:1 or greater was described above as necessary to achieve greater than 90% transesterification using as substrate soy flakes with a moisture content of 7.4%, it was found that using soy flakes with 0% moisture this ratio was reduced to 227:1, again at a sodium hydroxide concentration of 0.1 N and with reaction times of 5 to 10 h. Since the alkaline catalyst was dissolved in the alcohol phase, a reduction in the use of alcohol phase very desirably reduced the requirement for both alcohol and catalyst. We have also found it to be generally true that drier substrates gave higher levels of maximum attainable transesterification, surprisingly approaching or attaining 100% in the case of some feedstocks (see (2). (2) Numerous studies and general experience with biodiesel have demonstrated that the suitability of a fatty acid ester preparation for use as a diesel engine fuel depends on the degree of purity of the ester. To ensure fuel quality, standards have been adopted that specify the testing protocols for determination of the quality of an ester preparation, and the results that must be obtained if the preparation is to be acceptable fuel (i.e., is properly called "biodiesel"). Twenty kg of soy flakes with a moisture content of 0.8% was subjected to in situ transesterification at room temperature using the conditions of (1) above for dry substrate, with a 5.5 h reaction time. The liquid phase was recovered by filtration on Whatman No. 1 paper. The flake fraction was washed twice in 29 l of methanol, the washes being recovered by filtration and pooled with the reaction liquid. The final pooled liquids were adjusted to between pH 7 and 7.5 by the addition of concentrated hydrochloric acid. Methanol was removed under vacuum at 35-55° C. The resulting crude ester preparation was filtered over Whatman No. 1 paper and washed successively at room temp with 5 vols. tap water, 1/3 volume 0.5M NaCl, 0.03N NaOH, 1/10 volume 0.5 M NaCL and dried by the addition of 1/2000 volume of anhydrous sodium sulfate. The resulting ester preparation was analyzed as specified by the standards accepted for biodiesel in the United States (Standard Specification D-6751, American Society for Testing and Materials, Philadelphia, Pa.). The results of this assay are presented in Table 1:

TABLE 1

Properties of Fatty Acid Methyl Esters Synthesized from Soy Flakes by in situ Transesterification

| Property | Soy Flake Methyl Ester | Biodiesel Standard[a] (Max. allowed, unless noted) |
|---|---|---|
| Flash Point (° C.) | 160 | 130 (min.) |
| Water and Sediment (vol %) | 0 | 0.05 |
| Carbon Residue (wt %) | <0.010 | 0.05 |
| Sulfated Ash (mass %) | 0.000 | 0.020 |
| Kinematic Viscosity (cST, @ 40° C.) | 4.017 | 1.9-6.0 |
| Sulfur (wt %) | 0.00035 | 0.05 |
| Cloud Point (° C.) | 0.0 | Report |
| Copper Corrosion | 1a | 3 |
| Acid Number (mg KOH/g) | 0.04 | 0.80 |
| Free Glycerin (wt %) | 0.000 | 0.02 |
| Total Glycerin (wt %) | 0.071 | 0.240 |
| Phosphorus (wt %) | 0.0000 | 0.001 |
| Reduced Pressure Distillation (Temp, at 90% recovery, ° C.) | 350 | 360 |

[a]American Society for Testing and Materials, Philadelphia, PA. Standard Designation D 6751.

Thus, as shown in Table 1, the method described herein is capable of readily producing a fatty acid ester preparation that meets the existing specifications for biodiesel with little additional treatment. In particular, distillation of the fatty acid ester fraction was not necessary to recover a product of fuel-grade quality.

EXAMPLE 3

The lipid content of meat and bone meal is approximately 7-10% by weight. We determined that the fatty acids in the lipids in meat and bone meal can be converted at high efficiency to simple alcohol fatty acid esters by simple incubation in alcohol containing an alkaline catalyst. When 5 gm of meat and bone meal were incubated in sealed containers for 2 hours with 10 mL of 0.2 N sodium hydroxide solution in methanol at room temperature, an amount of fatty acid methyl ester surprisingly equal to approximately 75% of maximal theoretical was recovered. Conduct of this same reaction at 35° C. in sealed containers surprisingly increased the conversion of the lipid in meat and bone meal into fatty acid methyl ester to 100% of maximum theoretical. The reaction also occurred, with comparable high yields, at higher temperatures (e.g., 65° C.) although there is no practical reason for doing so since the reaction goes to quantitation at 35° C.; a pressure-resistant vessel would be needed at temperatures above the boiling point of the alcohol.

EXAMPLE 4

The triacylglycerol content of distiller's dried grains with solubles is in the region of 7-10 wt % and the moisture content is typically 7-10 wt %. We determined that the fatty acids in the lipids in DDGS are converted at high efficiency to simple alcohol fatty acid esters by reaction with alcohol containing an alkaline catalyst. Using a statistically designed experimental approach as described in Example 2, reaction conditions for maximum transesterification were identified. Reactions were conducted at 35° C. since high levels of reaction occurred at that temperature whereas reaction rates were poor at substantially lower temperatures. Fatty acid methyl ester (FAME) yields near maximum theoretical could be achieved with full-moisture DDGS by 0.5 h reaction with 20 ml of 0.25 N NaOH per 5 gm (dry wt equivalent) of DDGS. However, partial drying of the feedstock markedly reduced the reagent requirement. Thus, at 2.6 wt % moisture quantitative transesterification was achieved in 1.2 h reactions containing 14.0 ml of 0.40 N NaOH. With fully dry DDGS, however, transesterification never exceeded 25% of maximum theoretical.

Overview: As demonstrated previously (Kildiran, G., S. et al., J. Am. Oil Chem. Soc., 73: 225-228 (1996)) methanol itself is a poor vegetable oil extractant. We detected only negligible amounts of ester following a 4 h extraction of soy flakes with methanolic NaOH in a Soxhlet extractor. Presumably this is because the flake bed is exposed only to the methanol component under Soxhlet conditions. As shown here, however, incubation of soy flakes with alkaline methanol surprisingly results in the recovery of substantial amounts of fatty acid ester.

Our alkali-catalyzed method offers the advantages of (a) efficient operation using lipid-bearing materials such as soy flakes, meat and bone meal (MBM) and distiller's dried grains with or without solubles prepared by current industrial technology rather than requiring completely pulverized material, (b) use of less reagents and milder reaction conditions, and more importantly, (c) substantially higher ester yields. Although we have investigated primarily soy flakes, MBM and DDG/S as a substrates, we fully expect that the technique will be applicable to other oilseeds as well. In addition, this method should lend itself to continuous operation, a desirable format that also may increase ester yields.

All of the references cited herein are incorporated by reference in their entirety. Also incorporated by reference in their entirety are the following references: Freedman, B., et al., J. Am. Oil Chem. Soc., 61(10):1638-1643 (1984); Haas, M. J., et al., J. Am. Oil Chem. Soc., 77:373-379 (2000); Kildiran, G., S. et al., J. Am. Oil Chem. Soc., 73: 225-228 (1996); FR 2,784,116; WO 00/20540; EP 1,119,600. U.S. patent application Ser. No. 09/400,799, filed on 22 Sep. 1999, is incorporated by reference in its entirety. U.S. Provisional Patent Application Ser. No. 60/347,163, filed on 9 Jan. 2002, is incorporated by reference in its entirety; U.S. patent application Ser. No. 10/337,604, filed on 7 Jan. 2003, is incorporated by reference in its entirety Thus, in view of the above, the present invention concerns (in part) the following:

A method for producing fatty acid alkyl esters, comprising (or consisting essentially of or consisting of) transesterifying a feedstock containing lipid-linked fatty acids with an alcohol and an alkaline catalyst to form fatty acid alkyl esters, wherein (i) said feedstock has not been previously treated to release the lipid components of said feedstock and the yield of said fatty acid alkyl esters is at least about 75% (or at least about 80% or at least about 85% or at least about 90% or at least or at least about 95% or at least about 96% or at least about 97% or at least about 98% or at least about 99% or about 100%) of (theoretical) maximum or (ii) said feedstock has been previously treated to release lipid components and said feedstock contains residual lipid (e.g., < about 30% of its original content of lipids) and the yield of said fatty acid alkyl esters is at least 75% (or at least about 80% or at least about 85% or at least about 90% or at least or at least about 95% or at least about 96% or at least about 97% or at least about 98% or at least about 99% or about 100%) of (theoretical) maximum (or the feedstock used in the method is produced by a process involving treating an agricultural material (e.g., oilseeds) to produce free lipids and a by-product (i.e., the feedstock used in the present method) containing a small fraction (e.g., < about 30% by weight lipids) of the total lipids in the original untreated agricultural material).

The above method, wherein the feedstock has not been previously treated to release the lipid components of the feedstock. The above method, wherein the feedstock is a seed or fruit (or material derived from these). The above method, wherein the feedstock is soy, coconut, corn, cotton, flax, palm, rapeseed/canola, safflower, sunflower, or mixtures thereof. The above method, wherein the feedstock is soy. The above method, wherein the feedstock is coconut. The above method, wherein the feedstock is corn. The above method, wherein the feedstock is cotton. The above method, wherein the feedstock is flax. The above method, wherein the feedstock is palm. The above method, wherein the feedstock is rapeseed/canola. The above method, wherein the feedstock is safflower. The above method, wherein the feedstock is sunflower. The above method where the feedstock is distiller's dried grains with or without solubles. The above method, wherein the feedstock has been pre-treated to allow access of the alcohol and the alkaline catalyst to the interior of the feedstock.

The above method, wherein the feedstock has been previously treated to release lipid components and said feedstock contains residual lipid (e.g., < about 30% lipids) (or the feedstock used in the method is produced by a process involving treating an agricultural material (e.g., oilseeds) to produce free lipids and a by-product (i.e., the feedstock used in the present method) containing a fraction (e.g., < about 30% by weight lipids) of the total lipids in the original untreated agricultural material). The above method, wherein the feedstock is of plant or animal origin. The above method, wherein the feedstock is soy, coconut, corn, cotton, flax, palm, rapeseed/canola, safflower, sunflower, meat and bone meal, or mixtures thereof. The above method, wherein the feedstock is soy. The above method, wherein the feedstock is coconut. The above method, wherein the feedstock is corn. The above method, wherein the feedstock is cotton. The above method, wherein the feedstock is flax. The above method, wherein the feedstock is palm. The above method, wherein the feedstock is rapeseed/canola. The above method, wherein the feedstock is safflower. The above method, wherein the feedstock is sunflower. The above method, wherein the feedstock is meat and bone meal. The above method, wherein the feedstock is soy meal. The above method, wherein the feedstock excludes crude or refined isolated fats and oils from plant seeds or fruits or the lipids from animal products. The above method, wherein the feedstock excludes crude or refined isolated fats and oils from soy, coconut, corn, cotton, flax, palm, rapeseed/canola, safflower, sunflower, or the lipids from tallow, lard or fish oil.

The above method, wherein the fatty acid alkyl esters are fatty acid methyl esters or fatty acid ethyl esters.

The above method, wherein the alcohol is a $C_{1-4}$ alcohol.

The above method, wherein the alcohol is methanol, ethanol, isopropanol, or mixtures thereof.

The above method, wherein the alcohol is methanol, ethanol, or mixtures thereof.

The above method, wherein the alcohol is ethanol.

The above method, wherein the alcohol is methanol.

The above method, wherein the alkaline catalyst is a Group I or Group II hydroxide, alkoxide, or carbonate, or mixtures thereof.

The above method, wherein the alkaline catalyst is NaOH, KOH, sodium methylate, potassium methylate, sodium carbonate, potassium carbonate, or mixtures thereof.

The above method, wherein the alkali is NaOH, KOH, or mixtures thereof.

The above method, wherein the alkali is NaOH.

The above method, wherein the molar ratio of the alcohol: the alkaline catalyst is about $\leqq 500:1$ (e.g., about 67:1).

The above method, wherein the concentration of the alkaline catalyst is about $\geqq 0.05N$ (e.g., about 0.1N).

The above method, wherein the method utilizes about 0.04-about 25 ml of the alcohol per gram of the feedstock.

The above method, wherein the method utilizes a molar ratio of the alcohol: the feedstock glyceride content of 3.38-2178:1.

The above method, wherein the method utilizes about 2-about 10 ml of said alcohol per gram of the feedstock or about 4-about 9 or about 6-about 7.5.

The above method, wherein the method utilizes about 0.02-about 0.4 molar of alkali in the alcohol (or about 0.06-about 0.13 molar or about 0.08-about 0.11 molar).

The above method, wherein the reaction time of the method is about 1-about 12 hours (or about 8-about 9.5 hours or about 7-about 9 hours).

The above method, wherein the method is conducted at a reaction temperature of about 20°-about 70° C. (or about 20°-about 40° C. or about 20°-about 30° C.). Preferably, with full moisture soy flakes the reaction time is about 8 hours (e.g., 8 hours) at about 23° C. (e.g, 23° C.) or about 6 hours (e.g., 6 hours) at about 60° C. (e.g., 60° C.). However, as demonstrated in the Examples above, different feedstocks will display different optimum temperatures for transesterification. Clearly, the reaction can be successfully conducted at temperatures below the boiling point of the system at near atmospheric pressures. However, pressurized systems and higher temperatures could be employed in other embodiments of this invention.

The above method, wherein the produced fatty acid alkyl esters contain less than about 1000 mg free fatty acids)/g fatty acid alkyl esters (or less than about 800 mg FFA/g fatty acid alkyl esters or less than about 400 mg FFA/g fatty acid alkyl esters or less than about 200 mg FFA/g fatty acid alkyl esters or less than about 50 mg FFA/g fatty acid alkyl esters).

The above method, wherein the fatty acid alkyl esters contain less than about 5% weight basis of unreacted triacylglycerols, unreacted diacylglycerides, and unreacted monoacylglycerides (or less than about 1% weight basis of unreacted triacylglycerols, unreacted diacylglycerides, and unreacted monoacylglycerides).

A method for producing fatty acid alkyl esters, comprising (or consisting essentially of or consisting of) transesterifying a feedstock containing lipid-linked fatty acids with an alcohol and an alkaline catalyst to form fatty acid alkyl esters, wherein said feedstock has not been previously treated to release the lipid components of said feedstock and the yield of said fatty acid alkyl esters is at least 75% of maximum.

A method for producing fatty acid alkyl esters, comprising (or consisting essentially of or consisting of) transesterifying a feedstock containing lipid-linked fatty acids with an alcohol and an alkaline catalyst to form fatty acid alkyl esters, wherein said feedstock has been previously treated to release lipid components and said feedstock contains residual lipids and the yield of said fatty acid alkyl esters is at least 75% of maximum.

A method for producing fatty acid alkyl esters, comprising (or consisting essentially of or consisting of) transesterifying a feedstock containing lipid-linked fatty acids with an alcohol and an alkaline catalyst to form fatty acid alkyl esters, wherein said feedstock is distiller's dried grains (DDG) or distiller's dried grains with solubles (DDGS) and the yield of said fatty acid alkyl esters is at least 75% of maximum.

A method for producing fatty acid alkyl esters, comprising (or consisting essentially of or consisting of) transesterifying a feedstock containing lipid-linked fatty acids with an alcohol and an alkaline catalyst to form fatty acid alkyl esters, wherein (i) said feedstock has not been previously treated to release the lipid components of said feedstock or (ii) said feedstock has been previously treated to release lipid components and said feedstock contains residual lipid (e.g., <about 30% of its original content of lipids); said method produces at least about 75% of (theoretical) maximum of said fatty acid alkyl esters.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for producing fatty acid alkyl esters, comprising transesterifying a feedstock containing lipid-linked fatty acids with an alcohol and an alkaline catalyst to form fatty acid alkyl esters, wherein (I) said feedstock has not been previously treated to release the lipid components of said feedstock and the yield of said fatty acid alkyl esters is at least 90% of theoretical maximum or (ii) said feedstock has been previously treated to release lipid components and said feedstock contains residual lipids and the yield of said fatty acid alkyl esters is at least 75% of theoretical maximum; and wherein said feedstock excludes crude or refined isolated fats and oils from plant seeds or fruits or crude or refined animal products.

2. The method according to claim 1, wherein said feedstock has not been previously treated to release the lipid components of said feedstock.

3. The method according to claim 2, wherein said feedstock is a seed or fruit.

4. The method according to claim 2, wherein said feedstock is selected from the group consisting of soy, coconut, corn, cotton, flax, palm, rapeseed/canola, safflower, sunflower, distiller's dried grains with or without solubles, and mixtures thereof.

5. The method according to claim 2, wherein said feedstock is soy.

6. The method according to claim 2, wherein said feedstock is coconut or palm.

7. The method according to claim 2, wherein said feedstock is rapeseed/canola.

8. The method according to claim 2, wherein said feedstock is distiller's dried grains with or without solubles.

9. The method according to claim 2, wherein said feedstock has been pre-treated to allow access of said alcohol and said alkaline catalyst to the interior of said feedstock.

10. The method according to claim 1, wherein said feedstock has been previously treated to release lipid components and said feedstock contains residual lipids.

11. The method according to claim 10, wherein said feedstock has been previously treated to release lipid components and said feedstock contains < about 30% of the original content of lipids.

12. The method according to claim 10, wherein said feedstock has been previously treated to release lipid components and said feedstock contains < about 25% of the original content of lipids.

13. The method according to claim 10, wherein said feedstock has been previously treated to release lipid components and said feedstock contains < about 20% of the original content of lipids.

14. The method according to claim 10, wherein said feedstock has been previously treated to release lipid components and said feedstock contains < about 15% of the original content of lipids.

15. The method according to claim 10, wherein said feedstock is of plant or animal origin.

16. The method according to claim 10, wherein said feedstock is selected from the group consisting of soy meal, coconut meal, corn meal, cotton meal, flax meal, palm meal, rapeseed/canola meal, safflower meal, sunflower meal, meat and bone meal, and mixtures thereof.

17. The method according to claim 10, wherein said feedstock is meat and bone meal.

18. The method according to claim 10, wherein said feedstock is soy meal.

19. The method according to claim 1, wherein said feedstock excludes crude or refined isolated fats and oils from soy, coconut, corn, cotton, flax, palm, rapeseed/canola, safflower, sunflower, or tallow, lard or fish oil.

20. The method according to claim 1, wherein said fatty acid alkyl esters are fatty acid methyl esters or fatty acid ethyl esters.

21. The method according to claim 1, wherein said alcohol is a $C_{1-4}$ alcohol.

22. The method according to claim 1, wherein said alcohol is selected from the group consisting of methanol, ethanol, isopropanol, and mixtures thereof.

23. The method according to claim 1, wherein said alkaline catalyst is selected from the group consisting of Group I or Group II hydroxides, alkoxides, or carbonates, or mixtures thereof.

24. The method according to claim 1, wherein said alkaline catalyst is selected from the group consisting of NaOH, KOH, sodium methylate, potassium methylate, sodium carbonate, potassium carbonate, or mixtures thereof.

25. The method according to claim 1, wherein the molar ratio of said alcohol: said alkaline catalyst is about ≦500:1.

26. The method according to claim 1, wherein the concentration of said alkaline catalyst is about ≧0.05N.

27. The method according to claim 1, wherein said method utilizes about 0.04-about 25 ml of said alcohol per gram of said feedstock.

28. The method according to claim 1, wherein said method utilizes a molar ratio of said alcohol: said feedstock glyceride content of 3.38-2178:1.

29. The method according to claim 1, wherein said method utilizes about 2-about 10 ml of said alcohol per gram of said feedstock.

30. The method according to claim 1, wherein said method utilizes about 0.02-about 0.4 molar of alkali in said alcohol.

31. The method according to claim 1, wherein the reaction time of said method is about 1-about 12 hours.

32. The method according to claim 1, wherein said method is conducted at a reaction temperature of about 20°-about 70° C.

33. The method according to claim 1, wherein said fatty acid alkyl esters contain less than about 1000 mg free fatty acids/g fatty acid alkyl esters.

34. The method according to claim 1, wherein said fatty acid alkyl esters contain less than about 5% weight basis of unreacted triacylglycerols, unreacted diacylglycerides, and unreacted monoacylglycerides.

35. The method according to claim 1, wherein the yield of said fatty acid alkyl esters in (I) is at least about 80% of theoretical maximum.

36. The method according to claim 1, wherein the yield of said fatty acid alkyl esters in (I) is at least about 85% of theoretical maximum.

37. The method according to claim 1, wherein the yield of said fatty acid alkyl esters is at least about 90% of theoretical maximum.

38. The method according to claim 1, wherein the yield of said fatty acid alkyl esters is at least about 95% of theoretical maximum.

39. The method according to claim 1, wherein the yield of said fatty acid alkyl esters is at least about 96% of theoretical maximum.

40. The method according to claim 1, wherein the yield of said fatty acid alkyl esters is at least about 97% of theoretical maximum.

41. The method according to claim 1, wherein the yield of said fatty acid alkyl esters is at least about 98% of theoretical maximum.

42. The method according to claim 1, wherein the yield of said fatty acid alkyl esters is at least about 99% of theoretical maximum.

43. The method according to claim 1, wherein the yield of said fatty acid alkyl esters is at least about 100% of theoretical maximum.

44. A method for producing fatty acid alkyl esters, comprising transesterifying a feedstock containing lipid-linked fatty acids with an alcohol and an alkaline catalyst to form fatty acid alkyl esters, wherein said feedstock has not been previously treated to release the lipid components of said feedstock and the yield of said fatty acid alkyl esters is at least 90% of theoretical maximum; and wherein said feedstock excludes crude or refined isolated fats and oils from plant seeds or fruits or crude or refined animal products.

45. A method for producing fatty acid alkyl esters, comprising transesterifying a feedstock containing lipid-linked fatty acids with an alcohol and an alkaline catalyst to form fatty acid alkyl esters, wherein said feedstock has been previously treated to release lipid components and said feedstock contains residual lipids and the yield of said fatty acid alkyl esters is at least 75% of theoretical maximum; and wherein said feedstock excludes crude or refined isolate fats and oils from plant seeds or fruits or crude or refined animal products.

46. The method according to claim 1, wherein said method is conducted at a reaction temperature of about 20°-about 40° C.

47. The method according to claim 1, wherein said method is conducted at a reaction temperature of about 20°-about 30° C.

48. The method according to claim 1, wherein said method is conducted at a reaction temperature of 20°-40° C.

49. The method according to claim 1, wherein said method is conducted at a reaction temperature of 20°-30° C.

* * * * *